US 9,279,713 B2

(12) United States Patent
Ischdonat et al.

(10) Patent No.: US 9,279,713 B2
(45) Date of Patent: Mar. 8, 2016

(54) DETERMINATION OF BASIS WEIGHT OF A MATERIAL WEB USING A MICROWAVE SENSOR, WHEREBY THE DISTANCE BETWEEN THE MATERIAL WEB AND THE SURFACES OF THE MICROWAVE SENSOR IS BEING ADJUSTED TO A CONSTANT VALUE BY AIR CUSHIONS

(71) Applicant: Voith Patent GmbH, Heidenheim (DE)

(72) Inventors: Thomas Ischdonat, Bachhagel (DE); Ingolf Cedra, Heidenheim (DE); Oliver Kaufmann, Nattheim (DE)

(73) Assignee: Voith Patent GmbH, Heidenheim (DE)

( * ) Notice: Subject to any disclaimer, the term of this patent is extended or adjusted under 35 U.S.C. 154(b) by 384 days.

(21) Appl. No.: 13/917,844

(22) Filed: Jun. 14, 2013

(65) Prior Publication Data

US 2013/0277122 A1     Oct. 24, 2013

Related U.S. Application Data

(63) Continuation of application No. PCT/EP2011/071704, filed on Dec. 5, 2011.

(30) Foreign Application Priority Data

Dec. 16, 2010   (DE) .......................... 10 2010 063 232

(51) Int. Cl.
*G01G 17/02* (2006.01)
*G01N 22/00* (2006.01)
*G01G 9/00* (2006.01)
*G01N 33/34* (2006.01)

(52) U.S. Cl.
CPC ............... *G01G 17/02* (2013.01); *G01G 9/005* (2013.01); *G01N 22/00* (2013.01); *G01N 33/346* (2013.01)

(58) Field of Classification Search
CPC ...... G01G 9/005; G01G 17/02; G01N 33/346; G01N 22/00
See application file for complete search history.

(56) References Cited

U.S. PATENT DOCUMENTS 3,194,055 A     7/1965  Knobel
3,829,764 A *   8/1974  Bosisio ..................... 324/632
3,854,322 A    12/1974  Wood et al.
(Continued)

FOREIGN PATENT DOCUMENTS

DE    WO 2008-148596 A1 * 12/2008 ............... G10G 9/00
EP    1703275 A1    9/2006
GB    1367108       9/1974

OTHER PUBLICATIONS

International Search Report and Written Opinion dated Apr. 12, 2012 for International Application No. PCT/EP2011/071704 (10 pages).

*Primary Examiner* — Randy W Gibson
(74) *Attorney, Agent, or Firm* — Taylor IP, P.C.

(57) ABSTRACT

A device for determining the weight per unit area of a moving material web, in particular a fibrous material web includes at least one microwave sensor that has an element for coupling the microwaves and a reference element. The coupling element and the reference element are located at a distance from one another in such a way that the material web can be moved therebetween. At least one microwave sensor element, the coupling element and/or the reference element can be moved such that the distances between the material web and the elements can be adjusted for or during the measurement of the moving material web.

17 Claims, 2 Drawing Sheets

(56) References Cited

U.S. PATENT DOCUMENTS

| | | |
|---|---|---|
| 4,292,838 A | 10/1981 | Larsen |
| 4,528,507 A | 7/1985 | Domin et al. |
| 4,647,855 A | 3/1987 | Berglund |
| 4,678,915 A * | 7/1987 | Dahlquist et al. ......... 250/358.1 |
| 4,755,678 A | 7/1988 | Izatt et al. |
| 4,789,820 A * | 12/1988 | Parrent et al. ................ 324/640 |
| 4,890,054 A * | 12/1989 | Maeno et al. ................ 324/640 |
| 5,010,766 A * | 4/1991 | Typpo ............................ 73/159 |
| 5,770,949 A | 6/1998 | Sgro |
| 2006/0028213 A1* | 2/2006 | Typpo et al. ................. 324/640 |
| 2006/0208194 A1* | 9/2006 | Typpo et al. ............... 250/358.1 |
| 2007/0018657 A1* | 1/2007 | Nagata et al. ................ 324/636 |
| 2010/0141270 A1* | 6/2010 | Kaufmann et al. .......... 324/634 |
| 2013/0025350 A1* | 1/2013 | Nagata et al. .................... 73/73 |

\* cited by examiner

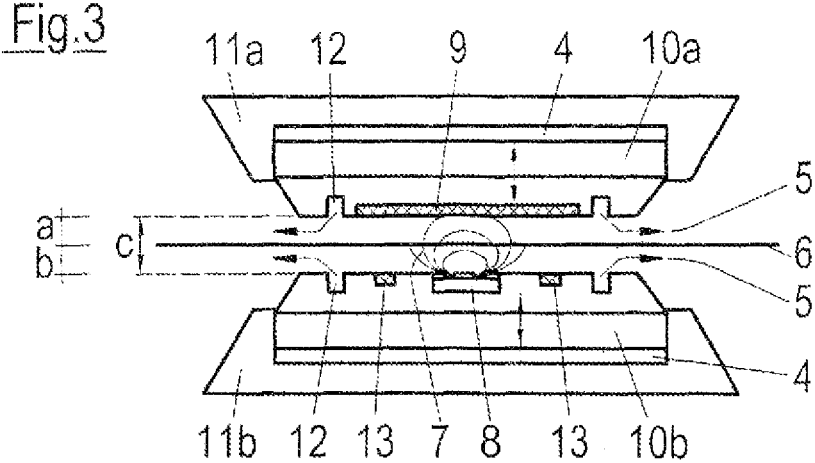
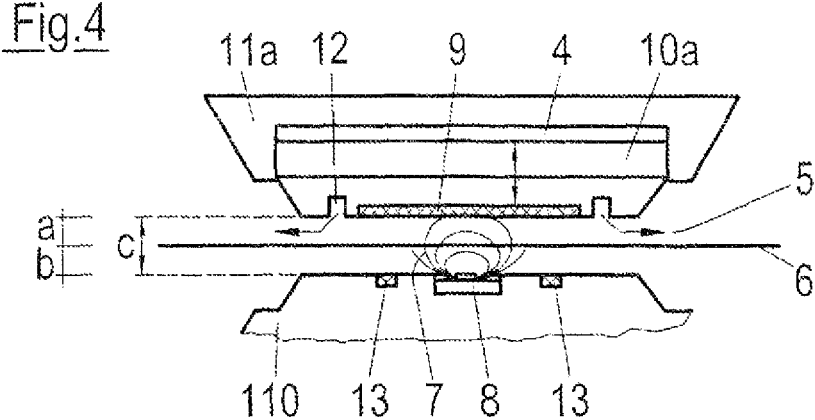
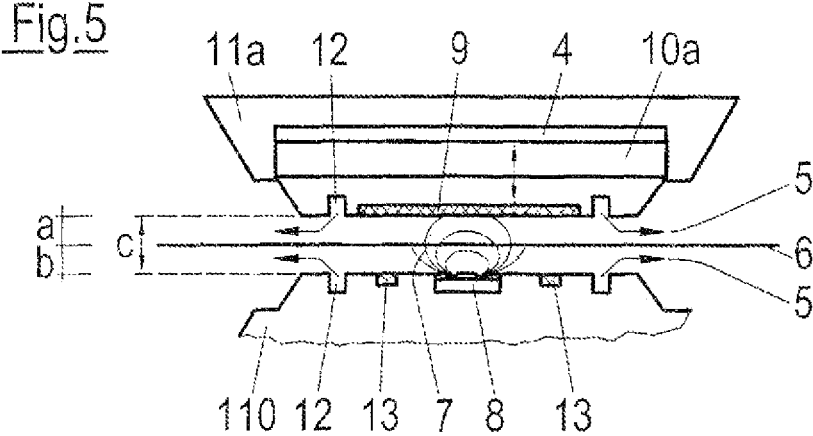

DETERMINATION OF BASIS WEIGHT OF A MATERIAL WEB USING A MICROWAVE SENSOR, WHEREBY THE DISTANCE BETWEEN THE MATERIAL WEB AND THE SURFACES OF THE MICROWAVE SENSOR IS BEING ADJUSTED TO A CONSTANT VALUE BY AIR CUSHIONS

CROSS REFERENCE TO RELATED APPLICATIONS

This is a continuation of PCT application No. PCT/EP2011/071704, entitled "DETERMINATION OF WEIGHT PER UNIT AREA OF A MATERIAL WEB USING A MICROWAVE SENSOR, THE DISTANCES BETWEEN THE MATERIAL WEB AND THE SURFACES OF THE MICROWAVE SENSOR BEING ADJUSTED TO A CONSTANT VALUE BY MEANS OF AIR CUSHIONS", Dec. 5, 2011 which is incorporated herein by reference.

BACKGROUND OF THE INVENTION

1. Field of the Invention

The present invention relates to a device and a method to determine the basis weight of a moving material web, in particular a fibrous web, including at least one microwave sensor which has an element for coupling the microwaves and a reference element, whereby the coupling element and the reference element are located at a distance from each other in a manner that the material web can be moved between them.

2. Description of the Related Art

Basis weight is generally understood to be the total weight of, for example a fibrous web, in other words the weight of all fibrous web components such as fibers, ash and water together. The fibrous web may be a paper web, tissue web or cardboard web.

Previous measurement technologies are usually based on the absorption of health hazardous radioactive radiation, so that such a measurement is always connected with considerable regulatory constraints.

The fundamental measuring principle is already known for example, from patent specification U.S. Pat. No. 4,755,678 by J. R. Izatt et. al. "Simultaneous measurement of moisture content and basis weight of paper sheet with sub-millimeter laser", or from the publication by E. Nyfors and P. Vainikainen "Industrial Microwave Sensors", published by Artech House Norwood 1989. One characteristic of such measurements is that the measurement signal is subjected to extreme intrinsic distance sensitivity.

Patent application EP 1 703 275A1 discloses a measuring device and a measuring method, and describes a microwave measurement which indeed considers this fact by measuring the distance and an appropriate signal correction, whereby the thus obtainable measurement results are too imprecise in practice.

What is needed in the art is a device and a method to determine the basis weight of web materials, which allows for a more precise basis weight measurement on a moving material web, using microwave radiation.

SUMMARY OF THE INVENTION

The present invention provides a device and a method to determine the basis weight of a moving material web. The device according to the present invention includes at least one microwave sensor which includes an element for coupling the microwaves, and a reference element, whereby at least one microwave sensor element, the coupling element and/or the reference element are arranged to be movable, so that the distances between the material web and the elements are adjustable for or during the measurement of the moving material web. The adjustment may occur for example through mechanical elements, whereby sensor element carriers on which the micro-sensor elements are mounted are moved parallel to each other in a carrier element guiding device.

The distances are adjusted in such a manner that the moving material web is held between the microwave sensor element carriers because of the Bernoulli-effect due to the dynamic pressure, so that both microwave sensor elements, the coupling element and the reference element do not come into contact with the material web. The adjustment can thereby occur on a calibration device for the measurement, or during measurement of the moving material web.

In addition, a distance measuring device is, for example, present with which the vertical distance between the coupling element and reference element which are arranged parallel to each other can be measured. A magnetic induction measuring device can be used for the distance measurement, whereby also other distance measurements are conceivable, for example with an optical measurement method.

Further, it is feasible for a control device to be present which controls the distances between resonator and web material, and between reference element and web material so that during the measurement the distance can be held constantly to a minimum, thereby achieving an increase in the accuracy of the measurement.

Additionally, the microwave sensor element carriers are kept at a distance from the material web using an air cushion, and the distances may be controlled by changes in the air cushion.

According to a first embodiment of the device according to the present invention, the distance between coupling element and web material, and between reference element and web material is adjusted or respectively controlled to 1 micrometer ($\mu$m) to 10,000 $\mu$m. The smaller the distance, the better are the measuring results.

In another embodiment of the device according to the present invention, especially precise distances can be obtained whereby at least one microwave sensor element, the coupling element and/or the reference element is movable in the direction of the material web by a first adjustable or controllable air cushion created through air pressure, and can be held at a distance from the material web by a second adjustable or controllable air cushion. Through this flexible arrangement, changes in the thickness of the material in particular can be compensated for, in particular at very small distances to the material web. To adjust the distances, actuators, in particular valves can be used with which the air cushion is modified or controlled.

For the measurement of the basis weight a relevant microwave resonator is used in a frequency range greater than 20 gigahertz (GHz). Moreover, a relevant microwave resonator can be used for the measurement of the basis weight, in a frequency range of 24 GHz to 24.25 GHz, 61 GHz to 61.5 GHz, 122 GHz to 123 GHz and 244 GHz to 246 GHz. Higher frequencies have the advantage that the permittivity of water is approximately the same as the permittivity of the other material web components, for example those of a fibrous web (see FIG. 1).

The measurement occurs, for example, on a moving material web by several of such stationary microwave sensors, distributed across the width of the fibrous web. Hereby at least the basis weight can advantageously be measured simultaneously through the plurality of the stationary microwave sensors which are distributed across the width of the fibrous web. Alternatively or additionally the measurement of the basis weight occurs on a moving web by at least one microwave sensor traversing across the width of the fibrous web.

According to a third embodiment of the device of the present invention, at least one coupling element includes a planar microwave resonator whose physical dimensions are in the range of the wavelength of the used primary radiation. The individual microwave resonators can be embedded in a ceramic and can be protected by a coating acting as a protection against contact with the material web.

The present invention also provides a method for determining the basis weight of a moving material web by a microwave sensor, including a resonator and a reference element which are arranged at a distance from each other in such a way that the material web can move between them, that the distance between resonator and web material, and between reference element and web material is adjusted independently of each other for or during measurement of the moving web material, and the basis weight is determined through the influence of the resonance curve relative to the set vertical distance between the resonator and reference element which are arranged parallel to each other.

According to a first embodiment of the method according to the present invention, the vertical distance between resonator and reference element is measured with a distance measuring device.

The distance between resonator and web material and between reference element and web material is, for example, adjusted to between 1 μm and 10,000 μm. The assignment of the absolute values occurs, for example, during calibration of the sensor.

The distances between resonator and web material and between reference element and web material and/or the distance between resonator and reference element are moreover advantageously controlled via a controller and the basis weight is determined through influencing of the resonance curve relative to the distance between coupling element and reference element, measured by the distance measuring device.

For the measurement of the basis weight a relevant microwave resonator is, for example, used in a frequency range greater than 20 GHz. Moreover, a relevant microwave resonator can be used for the measurement of the basis weight, in a frequency range of 24 GHz to 24.25 GHz, 61 GHz to 61.5 GHz, 122 GHz to 123 GHz and 244 GHz to 246 GHz.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 3 illustrates a basis weight sensor according to the present invention;

FIG. 4 illustrates an embodiment of a device according to the present invention; and FIG. 5 illustrates another embodiment of a device according to the present invention.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
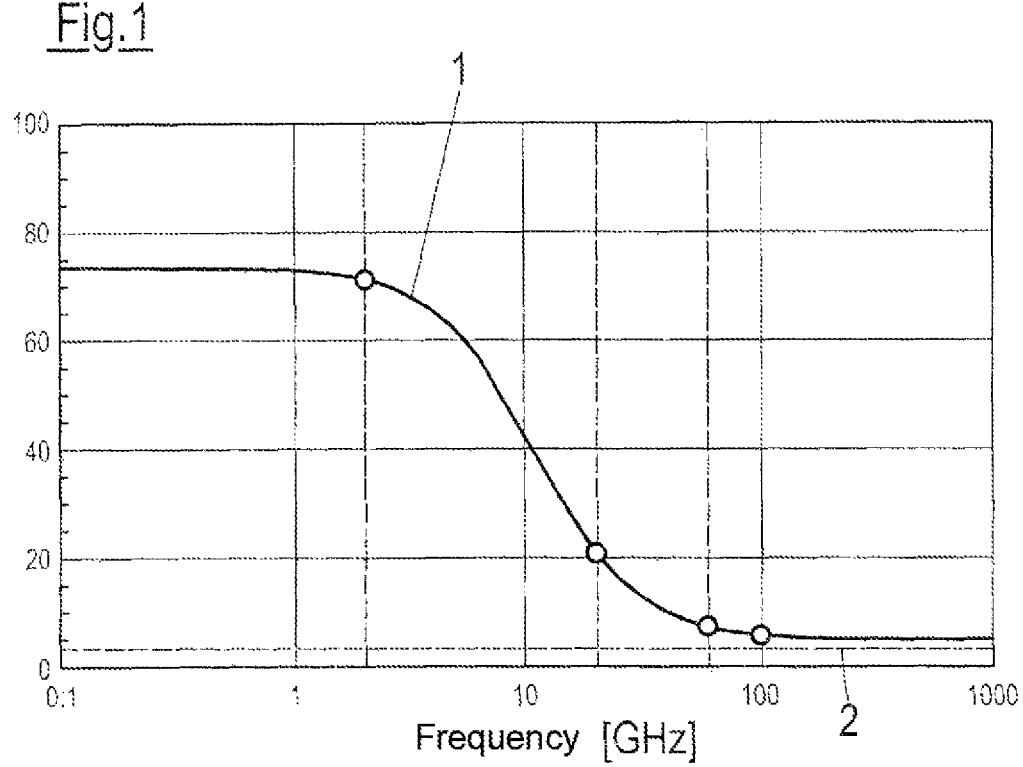
FIG. 1 illustrates progression of the permittivity of water and fibers.

Referring now to the drawings and more particularly to FIG. 1, there is shown a diagram showing the progression of the permittivity of water 1 and fibers 2. In measurements with microwaves the fundamental physical dimension is the permittivity $\epsilon r$. The progression of permittivity $\epsilon_r$ of water 1 and that of fibers 2 is illustrated over a frequency range of (0.1-1000) GHz at a temperature of 20° C.

The permittivity of paper, all components without the water portion, is approximately constant over the given frequency range ($\epsilon_{r\,paper}$~4-5). Since the entire basis weight is to be measured, the permittivities of all substances contained in the paper, primarily fibers, water and fillers must assume the same permittivity value, whereby with the exception of the filler titanium dioxide the permittivity of the other fillers is negligible.

As can be seen from the curve for water, the permittivity $\epsilon_r$ of water is strongly dependent upon the frequency. Only as of frequencies>20 GHz the permittivity $\epsilon_r$ of water is in the same range as that for fibers. This is the reason that higher frequencies must be used for measuring the overall basis weight.

For measuring the basis weight it is thereby necessary to locate a frequency range in which all substances contained in the fibrous web or respectively the paper, have a more or less identical permittivity. This ensures that the fibrous web or respectively the paper can be regarded as a substantially homogeneous object of measurement. This measurement range is within frequency ranges greater than 20 GHz, for example within frequency ranges greater than 100 GHz.

Figure 2:
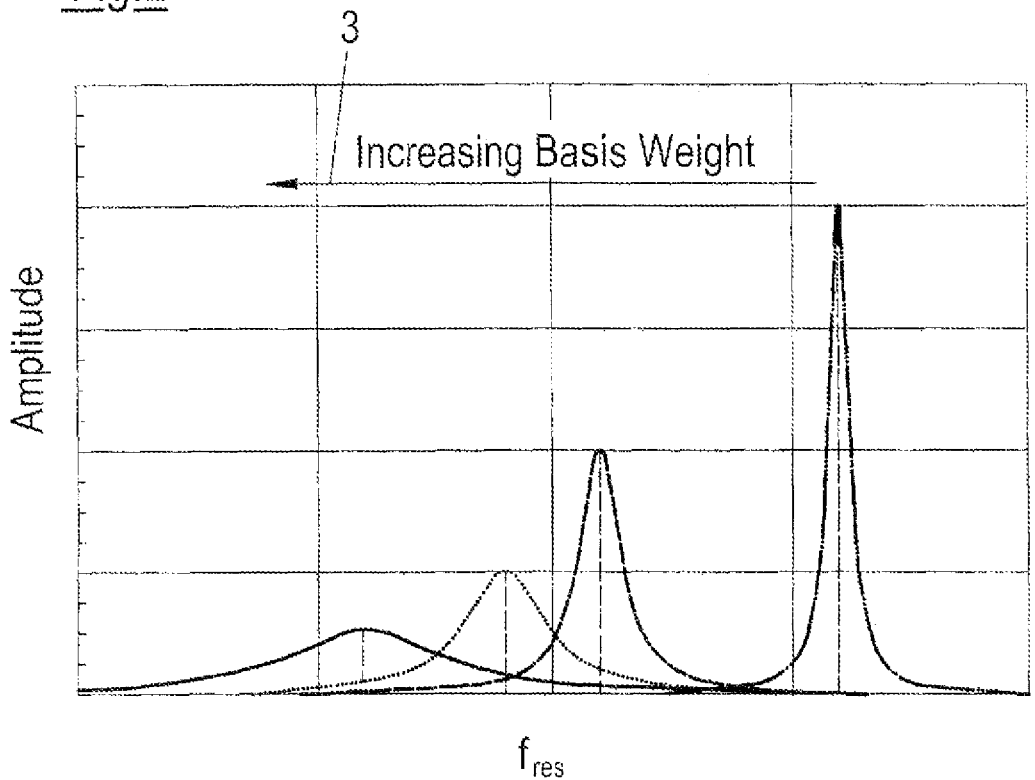
FIG. 2 illustrates progression of the resonance frequency elative to the basis weight.

One suitable method of determining the permittivity and thereby the basis weight is a measurement of the resonance frequency of a microwave resonator. Under the above condition, the resonance frequency is clearly dependent upon the basis weight, as can be seen in FIG. 2. The higher the basis weight is, the lower is the amplitude of the resonance frequency.

The determining factor in this type of measurements is the permittivity of the material which is to be examined, with which the resonator interacts. The permittivity determines the frequency and damping behavior of the resonator. A displacement of the resonance frequency, as well as a change in the resonance width occurs thereby due to the different materials with which the resonator interacts. At a greater permittivity the resonance frequency changes to lower frequencies, whereas the width of the resonance curve increases.

A great disadvantage of the resonance method is that the measured resonance frequency is strongly dependent upon the distance of the resonator to the paper. Ideal would be a contact with the paper web. However due to technological reasons it is imperative that this is avoided. If the sensor were to touch the paper web it would tear.

Referring now to FIG. 3, there is illustrated an inventive basis weight sensor. The sensor includes a resonator 8 and a reference element 9 which are respectively arranged on a carrier element 10*a*, 10*b*. Carrier elements 10*a*, 10*b* are guided—parallel to each other—in a carrier element guiding device 11*a*, 11*b* in such a way that distance c between resonator 8 and reference element 9 is changeable through the independent displacement of the carrier elements 10*a*, 10*b*.

Carrier elements 10*a*, 10*b* are pressed against material web 6 by a first air cushion 4. A second air cushion 5 ensures that the distance a, b to material web 6 is maintained, so that a material web 6 can pass between carrier elements 10a, 10b.

To produce air cushion 5, carrier elements 11a, 11b are equipped accordingly with nozzle openings 12 which are supplied with compressed air from a compressed air source. Second air cushion 4 is producible between carrier plate 10a, 10b and carrier element 11a, 11b so that carrier element 11a, 11b can be moved in a guide mechanism for carrier elements 11a, 11b.

Air cushions 4, 5 may be controlled for example through valves (actuators) in such a way that distance a, b, c between resonator 8 and reference element 9 and/or between resonator 8 and web material 6, as well as between reference element 9 and web material 6 can be adjusted as desired. Distances a, b, c can be selected and controlled differently, depending upon the paper technological application.

The distance c between resonator 8 and reference material 9 can be between 1 μm and 10,000 μm. For measurement of the distance, a distance measuring device 13 is also installed which measures distance c via magnetic induction.

Due to the fact that resonator 8 and reference element 9 are mounted to be movable and their distance a, b to the paper web is controlled by the air cushion and can be set to a minimum value, and distance c is measured, it is ensured that there is no contact with paper web 6.

Two additional embodiments of the device of the present invention are shown in FIGS. 4 and 5. In these embodiments only the upper carrier elements 11a are arranged movably parallel to the material web. Lower carrier elements 110 are arranged opposite upper carrier element 11a in a fixed position.

In the embodiment of the present invention illustrated in FIG. 4 the moving material web is lifted off the lower microwave sensor element carrier only due to the Bernoulli-effect. The adjustment of the distances occurs through control of air cushions 4, 5 through which distance c, as well as distances a and b can be adjusted or respectively controlled.

The difference between the embodiments in FIG. 4 and FIG. 5 is that in FIG. 5 nozzle openings 12 are arranged in lower carrier element 110. Therefore, an air cushion 5 can be established here, which lifts material web 6 off of carrier element 110 and distances a, b and c are controllable in interaction with air cushions 4, 5.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A device to determine a basis weight of a moving material web, said device comprising:
    at least one microwave sensor having a coupling element configured for coupling microwaves and a reference element, said coupling element and said reference element located at a distance from each other so that the material web passes therebetween, said coupling element and said reference element being moveable such that a distance between the material web and each of said coupling element and said reference element is adjustable and at least said distance between said material web and said reference element is set to a minimum value for or during measurement of the moving material web.

2. The device according to claim 1, wherein said moving material web is a fibrous web.

3. The device according to claim 1, further comprising a distance measuring device configured for measuring a vertical distance between said coupling element and said reference element, said coupling element and said reference element being arranged parallel to each other.

4. The device according to claim 3, wherein said distance measuring device is a magnetic induction measuring device.

5. The device according to claim 4, further comprising a controller for adjusting a distance between the moving material web and said coupling element and said reference element during a measurement of the moving material web.

6. The device according to claim 1, wherein a distance between said coupling element and the moving material web and a distance between said reference element and the web material is controlled to between 1 micrometer (μm) and 10,000 μm.

7. The device according to claim 1, further comprising a first air cushion configured to be controlled or adjustable and a second air cushion configured to be controlled or adjustable, said first air cushion configured for moving at least one of said coupling element, said reference element and said at least one sensor and said second air cushion configured for holding at least one of said coupling element, said reference element and said at least one microwave sensor at a distance from the moving material web.

8. The device according to claim 1, further comprising a plurality of actuators configured for adjusting distances.

9. The device according to claim 8, wherein said actuators are a plurality of valves.

10. The device according to claim 1, further comprising a microwave resonator configured for measuring the basis weight at a frequency range greater than 20 gigahertz (GHz).

11. A method for determining the basis weight of a moving material web, the method comprising the steps of:
    providing at least one microwave sensor including a coupling element configured for coupling microwaves and a reference element, said coupling element and said reference element being parallel to each other and located at a distance from each other such that the moving material web moves therebetween, said coupling element and said reference element being moveable;
    measuring the moving material web;
    adjusting distances of at least one of said coupling element, said reference element, and said at least one microwave sensor to a value for or during said measuring step, wherein at least a distance between said material web and said reference element is set to a minimum value; and
    determining the basis weight through a resonance curve relative to a set vertical distance between said coupling element and said reference element.

12. The method according to claim 11, wherein the moving material web is fibrous web.

13. The method according to claim 11, further comprising the step of measuring a distance between a resonator and said reference element with a measuring device.

14. The method according to claim 13, wherein a distance between the moving material web and said coupling element and said reference element with a controller and said step of determining the basis weight further comprising the step of measuring a distance between said coupling element and said reference element with a distance measuring device.

15. The method according to claim 14, further comprising the step of adjusting a distance between said resonator and the moving material web and between the reference element and the moving material web to 1 micrometer (μm) to 10,000 μm.

16. The method according to claim 15, further comprising the steps of:
   using a first air cushion created with air pressure to move at least one of said coupling element, said reference element and said at least one microwave sensor in a direction of the material web using air pressure, said first air cushion being controllable or adjustable; and
   using a second air cushion created with air pressure to hold said at least one of said coupling element, said reference element and said at least one microwave sensor at a distance from the moving material web.

17. The method according to claim 11, further comprising the step of using a microwave resonator at a frequency range greater than 20 gigahertz (GHz) to determine the basis weight.

* * * * *